United States Patent [19]

Graham et al.

[11] Patent Number: 4,827,550
[45] Date of Patent: May 9, 1989

[54] REMOVABLE HEAD MECHANISM FOR AUTOMATIC CLEANING DEVICE

[75] Inventors: Cleve A. Graham, Simi Valley, Calif.; John Trenary, Lilburn, Ga.

[73] Assignee: Dental Research Corporation, Tucker, Ga.

[21] Appl. No.: 191,859

[22] Filed: May 4, 1988

Related U.S. Application Data

[63] Continuation of Ser. No. 891,274, Jul. 29, 1986, abandoned, which is a continuation-in-part of Ser. No. 743,100, Jun. 10, 1985, abandoned.

[51] Int. Cl.⁴ ............................................. A46B 13/02
[52] U.S. Cl. ...................................... 15/22 R; 15/28; 403/326; 433/131
[58] Field of Search ................ 15/22 R, 22 A, 23, 24, 15/28, 29, 97 R; 433/118, 122, 126, 131; 81/438, 439, 440; 51/170 TL; 403/326, 368, 361, 375; 366/332

[56] References Cited

U.S. PATENT DOCUMENTS

| | | |
|---|---|---|
| 793,587 | 6/1905 | Johnson . |
| 947,908 | 2/1910 | Heglar . |
| 1,212,001 | 1/1917 | Baxter . |
| 1,476,433 | 12/1923 | Vandervoort . |
| 1,517,320 | 12/1924 | Stoddart . |
| 1,557,244 | 10/1925 | Domingue . |
| 1,712,579 | 5/1929 | Nichols . |
| 2,044,863 | 6/1936 | Sticht . |
| 2,140,307 | 12/1938 | Belaschk et al. . |
| 2,172,624 | 9/1939 | Robert . |
| 2,196,667 | 12/1937 | Moseley . |
| 2,215,031 | 9/1940 | Elmore . |
| 2,448,614 | 9/1948 | Mirus ...................................... 15/23 |
| 2,476,154 | 7/1949 | Lohs . |
| 2,598,275 | 5/1952 | Lakin . |
| 2,682,066 | 6/1954 | Keely . |
| 2,799,878 | 7/1957 | Brausch . |
| 2,922,656 | 1/1960 | Belloli . |
| 3,029,451 | 4/1962 | Barr ........................................ 15/23 |
| 3,043,614 | 7/1962 | Eichmann . |
| 3,103,679 | 9/1963 | Clemens . |
| 3,152,810 | 10/1964 | Brinkman . |
| 3,160,902 | 12/1964 | Aymar . |
| 3,178,754 | 4/1965 | Cleverdon . |
| 3,240,077 | 3/1966 | Smith . |
| 3,242,516 | 3/1966 | Cantor . |
| 3,281,878 | 11/1966 | Roiz . |
| 3,400,417 | 9/1968 | Moret . |
| 3,577,579 | 5/1971 | Duve et al. . |
| 3,595,126 | 7/1971 | Norton . |
| 3,802,420 | 4/1974 | Moffat et al. ........................... 15/28 |
| 4,156,620 | 5/1979 | Clemens . |
| 4,274,173 | 6/1981 | Cohen . |
| 4,365,376 | 12/1982 | Oda et al. ............................. 15/22 R |
| 4,603,448 | 8/1986 | Middleton et al. . |

FOREIGN PATENT DOCUMENTS 634607 8/1936 Fed. Rep. of Germany .
1114464 10/1961 Fed. Rep. of Germany .

(List continued on next page.)

*Primary Examiner*—Edward L. Roberts
*Attorney, Agent, or Firm*—Jones, Askew & Lunsford

[57] ABSTRACT

A cleaning apparatus is provided for transmitting powered motion to an operating member having a removable head mechanism contained within a hollow housing. A motorized base, including a base drive shaft, is locked onto a head drive shaft of the removable head mechanism in response to axial movement of the base drive shaft into the housing. The head mechanism comprises a collet having outwardly radiating arms and inwardly extending feet at the lower end of the collet and a rack at the upper end. The rack engages rotatable gears containing tufts of filaments. The base drive shaft defines a shoulder and a tip at the upper end which is received into the collet. A sleeve, retained within the head mechanism by the inner dimensions of the hollow housing, receives the outwardly radiating arms and compresses them over the tip of the base causing the feet to engage the shoulder. Once locked onto the head mechanism, the axial movement of the base drive shaft causes rotation and counter-rotation of the gears and the tufts mounted within the gears. Unlocking of the shafts is accomplished by pulling the head mechanism away from the base. The rotational movement of the tufts is useful for cleaning surfaces such as teeth.

34 Claims, 6 Drawing Sheets

FOREIGN PATENT DOCUMENTS

| | | |
|---|---|---|
| 2201745 | 10/1972 | Fed. Rep. of Germany . |
| 2215799 | 10/1972 | Fed. Rep. of Germany . |
| 2363364 | 12/1973 | Fed. Rep. of Germany . |
| 2263432 | 5/1974 | Fed. Rep. of Germany . |
| 1632386 | 4/1980 | Fed. Rep. of Germany . |
| 800826 | 1/1936 | France . |
| 934142 | 10/1946 | France . |
| 197806 | 10/1976 | France . |
| 2368854 | 5/1978 | France . |
| 480510 | 5/1953 | Italy . |
| 0033753 | 3/1978 | Japan .................................. 15/22 R |
| 363635 | 3/1959 | Switzerland . |
| 190787 | 10/1921 | United Kingdom . |
| 500517 | 2/1939 | United Kingdom . |
| 1081021 | 8/1967 | United Kingdom . |

Fig_3

Fig_7

Fig_8

Fig_11

Fig_10

REMOVABLE HEAD MECHANISM FOR AUTOMATIC CLEANING DEVICE

This application is a continuation of Ser. No. 06/891,274, filed July 29, 1986, now abandoned, which is a continuation-in-part of Ser. No. 06/743,100, filed June 10, 1985, now abandoned.

TECHNICAL FIELD

The present invention relates to an apparatus for transmitting powered motion to an operating member having a removable head mechanism, and more particularly relates to an automatic cleaning device such as a peridontal device having a removable toothbrush attachment.

BACKGROUND OF THE INVENTION

Power tools have been available for many years for a variety of different applications including cleaning or polishing. Automated cleaning devices such as floor polishers, pot scrubbers, facial massagers, fingernail polishers and electric toothbrushes utilize a rapidly moving brush-like device at the end of a motorized drive shaft. The drive shaft of these devices either spins continuously in one direction or oscillates back and forth, and the brush device moves with the drive shaft.

Originally, the brush members of such power tools were permanently affixed to the drive shaft. Eventually, brush attachments were devised so that, when the scrubbing surface of the attachment lost its abrasive qualities, the attachment could be inexpensively replaced instead of replacing the entire unit. However, these attachments did not contain any independently moving parts, and the brush movement was limited to the rotational or alternating movement of the drive shaft.

U.S Pat. No. 4,156,620 discloses an apparatus for cleaning teeth wherein the brush portion of the apparatus contains a number of tufts which independently rotate and counter-rotate in response to the axial movement of a single drive shaft. This unusual brush movement has been shown to be successful in the prevention of cavities and peridontal problems caused by bacterial plaque.

U.S. patent application Ser. No. 743,100 describes a related cleansing apparatus which can be used for various cleaning applications including use by the dental patient in the home as a plaque-removing device. This apparatus is battery operated and sits in a recharging base until used.

The automatic cleaning device of U.S. Pat. No. 4,156,620 and U.S. patent application Ser. No. 743,100 is constructed as a one-piece unit. Therefore, if different brushes or replacement brushes are desired, the consumer will be forced to purchase an entire unit for each new brush or replace the tufts one at a time; and, if the device is used as a home plaque-removal instrument, separate units will be required by each user in any particular household.

Providing the described automatic cleaning device as a two-piece unit with a separate brush-containing head mechanism and a power-driven base presents special problems. Unlike conventional power tools, the brush portion of the above-described automatic cleaning device contains moving parts. Therefore, a simple, snap-on, brush-containing head member would be unable to translate the movements of the power drive contained within the base to the movable brushes contained within the head. Thus there is a need for a connection that can securely attach the powered drive shaft within the base to a reciprocating brush driving means within the brush-containing head.

SUMMARY OF THE INVENTION

The present invention satisfies the need for a two-piece automatic cleaning device with a removable head mechanism. The user can use the same base assembly with any of a number of different head mechanisms, so that the device can be used in a variety of cleansing applications. In addition, by purchasing several toothbrush head mechanisms, entire households can share the use of a single plaque-removing device.

Generally described, the present invention provides a removable head mechanism, for use with a base having a base drive shaft extending therefrom, comprising a hollow housing, a head drive shaft slidably mounted within the housing, and means for connecting the base drive shaft to the head drive shaft in response to axial movement of the base drive shaft into the housing. More particularly described, the present invention provides a removable head mechanism, for use with a base having a base drive shaft extending therefrom, in which the base drive shaft defines a shoulder spaced inwardly from the end of the shaft, and the removable head mechanism comprises a hollow housing, a head drive shaft slidably mounted within the housing, a flexible arm mounted for movement with the head drive shaft with an inwardly extending foot at the end of the arm, and locking means for selectively moving the arm between an unlocked position radially outwardly of the shoulder defined by the base drive shaft and a locked position in which the foot engages the shoulder.

Preferably, the locking means comprises a hollow sleeve, large enough to receive the head drive shaft and the flexible arm, wherein the act of sliding the flexible arm into the sleeve causes the foot to flex inwardly to engage the shoulder of the base drive shaft. Also provided is means for removing the flexible arm from the sleeve, causing the foot to be released from the shoulder.

Somewhat more particularly described, the housing of the head mechanism defines an interior ridge or shoulder positioned in the path of the hollow sleeve, causing the retention of the hollow sleeve as axial movement of the base drive shaft causes the head drive shaft to slidably enter the hollow sleeve, which in turn causes the foot to engage the shoulder of the base drive shaft. The removable head mechanism also includes unlocking means which comprises a sleeve retainer ring with an opening larger than the head drive shaft, but smaller than the external diameter of the sleeve. The sleeve retainer is positioned so that, as the head mechanism is detached from the base, the sleeve abuts the sleeve retainer and the sleeve is slidably removed from the arm, releasing the foot from the shoulder of the base drive shaft.

Preferably, the base of the present invention comprises a base drive shaft, means for driving the base drive shaft, a bearing through which the base drive shaft passes, and a seal through which the base drive shaft passes.

The present invention also provides a recess for receiving a work-engaging member operatively connected to the head drive shaft. A plate covers the recess and defines a bearing for receiving the work-engaging member, and a tab extends across the path of movement of the head drive shaft with an opening in the tab through which the head drive shaft passes.

It will thus be seen that the present invention provides an apparatus for transmitting powered motion to an operating member, comprising a base having a base drive shaft extending therefrom, a removable head mechanism having a head drive shaft slidably mounted within a hollow housing, and means for connecting the base drive shaft to the head drive shaft responsive to axial movement of the base drive shaft in the housing.

Thus, it is an object of the present invention to provide a removable head mechanism for an automatic cleaning device.

It is a further object of the present invention to provide a head mechanism with moving parts that can be driven by a head drive shaft connected to a powered base drive shaft.

It is a further object of the present invention to provide a head mechanism that can be quickly and easily attached and detached from a base without the use of tools.

It is a further object of the present invention to provide an apparatus with a head mechanism, containing moving parts, removably attached to a power-driven base.

It is a further object of the present invention to provide a power-driven base which can be removably attached to a variety of head mechanisms.

It is a further object of the present invention to provide a removable head mechanism capable of containing rotating tuft filaments.

Other objects, features, and advantages of the present invention will become apparent in the following detailed description of preferred embodiments of the invention, when taken in conjunction with the drawing and the appended claims.

DETAILED DESCRIPTION

Figure 1:
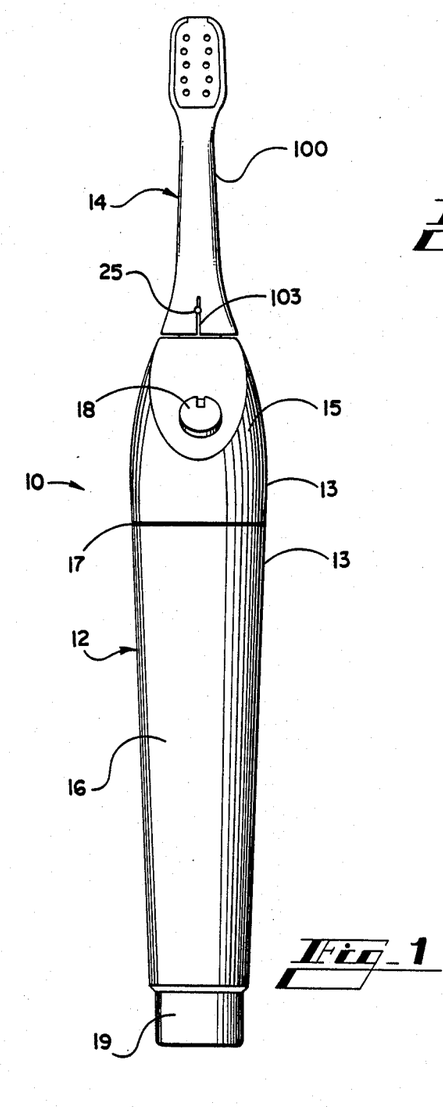
FIG. 1 is a pictorial view of a cleaning apparatus embodying the present invention.

Referring now in more detail to the drawing, in which like reference numerals represent like parts throughout the several views, FIG. 1 shows a cleaning device 10 embodying the present invention. The preferred embodiment of the cleaning device includes a base 12 removably attached to a head mechanism 14.

Figure 2:
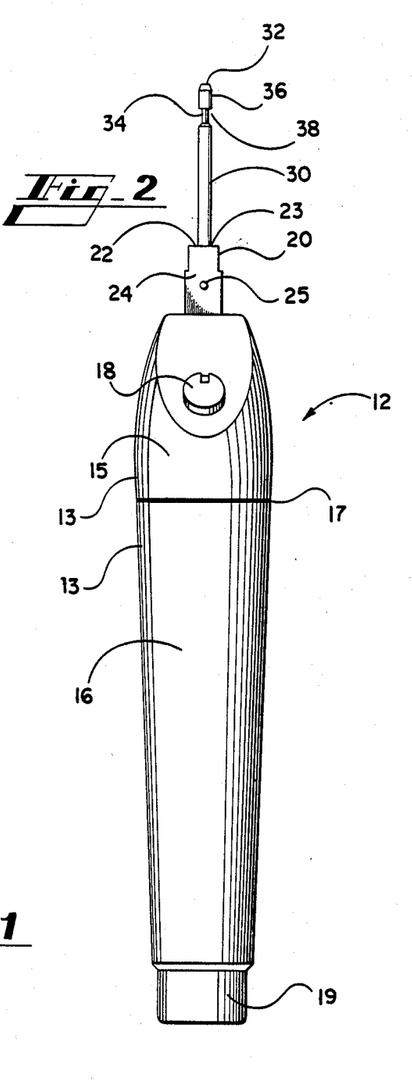
FIG. 2 is a pictorial view of the base of the present invention with the removable head mechanism removed.

As best shown in FIG. 2, the base 12 comprises a hollow housing 13 which may be fabricated out of molded plastic or a similar material. The base 12 is comprised of an upper portion 15 and a lower portion 16. The upper and lower portions 15 and 16 are joined together at 17 so that the resulting seal is waterproof. The foot 19 of the lower portion 16 of the base 12 is designed to fit within a recharging device (not shown). A recharging apparatus suitable for use in the base 12 is described in application Ser. No. 743,100, which is expressly incorporated herein by reference in its entirety. A power switch 18 is connected to the motorized driving means of the device, shown in FIG. 6, and lies adjacent to the external housing of the upper portion 15 of the base 12 in a position where it can be easily manipulated by the thumb of a hand grasping the cleaning device 10.

In the preferred embodiment of the present invention, a hollow neck 20 extends upwardly from the upper portion 15 of the housing 13 of the base 12. The neck 20 defines a flat, D-shaped top surface 22 including a mouth 23 opening into the interior of the neck, and a flat front surface 24. A round headed screw 25, preferably metallic, is driven into the flat front surface 24 to aid in securing the removable head mechanism 14 to the base 12. In an alternative embodiment (not shown) the neck 20 of the base 12 is cylindrical with a chamfer or beveled edge upon which the removable head is secured only by friction.

A base drive shaft 30, having an outermost end 32, extends through the mouth 23 of the neck 20 of the base 12 and includes an annular indented region 34 spaced a short distance from the end 32 of the shaft 30, creating a tip 36 and a shoulder 38 facing the upper portion 15 of the base housing 13. The tip 36 is tapered at the end 32 to facilitate insertion into the head mechanism 14.

As shown in FIGS. 3, 4, 5, and 6, the base drive shaft 30 extends downwardly into the neck 20 where it passes through a seal 40 which has a cylindrical collar 42 closely fitting between the mouth 23 and the shaft 30. The seal 40 prevents fluids or dust from entering the housing 13 while permitting movement of the shaft 30 with respect to the housing 13. In the embodiment shown, such movement is reciprocation out of and into the housing. Below the seal 40, a cylindrical bearing 50 is secured within the neck 20. The bearing 50 receives the shaft 30 for sliding movement within the bearing. Below the bearing 50 a shaft retaining bracket 60 is positioned in the housing 13. The bracket 60 defines at its upper end a cylindrical collar 62 shaped to be matingly received within the neck 20, where the collar 62 assists in retaining the bearing 50 within the neck. The penetration of the collar 62 into the neck 20 is limited by a flange 64 extending outwardly beyond the collar. A lower bearing member 66 is held in spaced apart relation to the flange 64 by a slotted tube 68. A pair of wings 65 and 67 adjacent to the slotted tube 68 aid in positioning the slotted tube in the center of the housing 13. The drive shaft 30 passes freely through the collar 62 and flange 64 and is slidably received by the lower bearing 66. Thus, the path of the drive shaft 30 is defined by the bearings 50 and 66.

Figure 6:
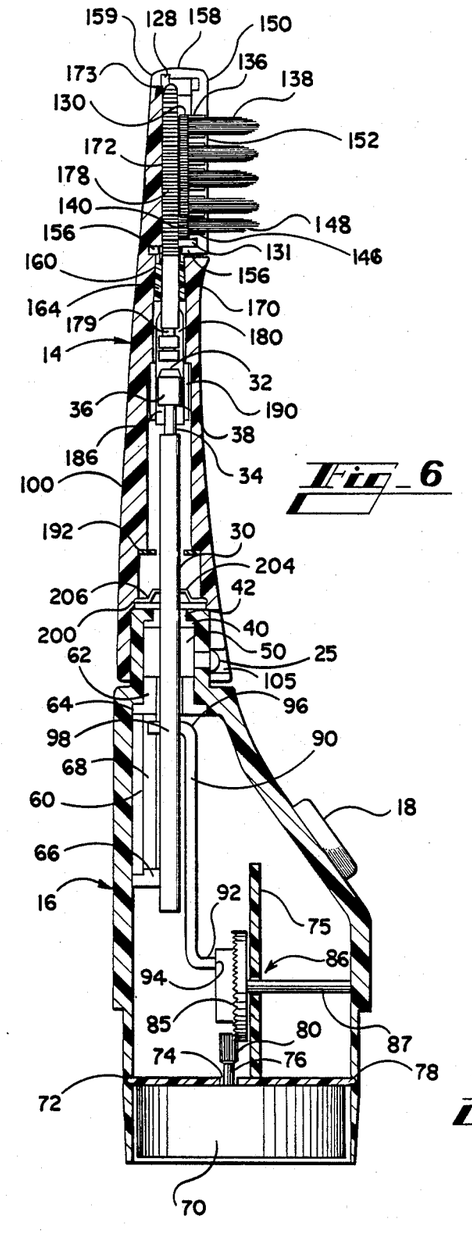
FIG. 6 is a side vertical cross sectional view taken along line 6—6 of FIG. 4 with the base drive shaft in the extended position.

A motor 70 and transmission gears 80 and 85, shown in FIG. 6, of the type shown in application Ser. No. 743,100, are mounted within the base housing 13 below the rear bearing member 66, and are drivingly connected to the drive shaft 30. The motor 70 is essentially cylindrical, having a circular or D-shaped top plate 72 with a central bore 74. A vertical support member 75 extends vertically at right angles from the top plate 72 of the motor 70. A gear drive shaft 76 extends from the motor through the bore 74. The external diameter of the top plate 72 is equal to the internal diameter of the base housing 16 and is press fit into a groove 78 in the base housing 16. The motor 70 is thus suspended within the base housing 16 from the attached top plate 72.

A pinion gear 80 is mounted at the uppermost portion of the gear drive shaft 76 and meshes with a crown or face gear 85. The face gear 85 is rotatably mounted on a horizontal shaft 87 which passes through a central bore 86 in the vertical support member 75. When the motor 70 is turned on by operation of the switch 18, rotation of the pinion gear 80 causes rotation of the face gear 85 about a horizontal axis perpendicular to the longitudinal axis of the base housing 13.

A crank arm 90 connects the face gear 85 to the base drive shaft 30. A lower end 92 of the crank arm 90 is pivotally attached eccentrically to the face gear at a lower pivot joint 94. An upper end 96 of the crank arm 90 is pivotally connected to the base drive shaft 30 at an upper pivot joint 98 located between the flange 64 and the rear bearing 66. When the motor is turned on, the rotation of the face gear 85 causes the lower end 92 of the crank arm 90 to move in a circular path defined by the movement of the face gear. The connection at the upper pivot joint 98 and the restrictions of the cylindrical bearing 50 and rear bearing 66 translate the circular movement of the crank arm 90 into reciprocating axial movement of the base drive shaft 30 described in more detail below.

Figure 3:
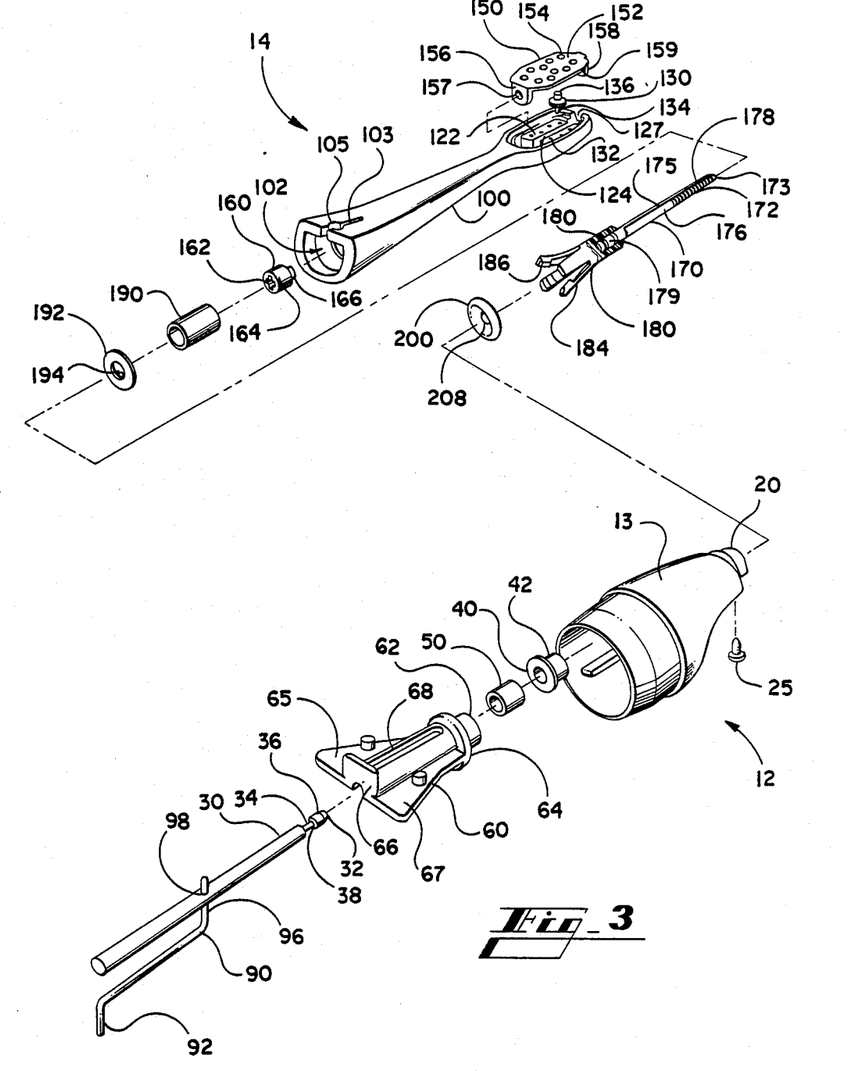
FIG. 3 is an exploded perspective view of the removable head mechanism and portions of the base of the cleaning apparatus shown in FIG. 1.
Figure 9:
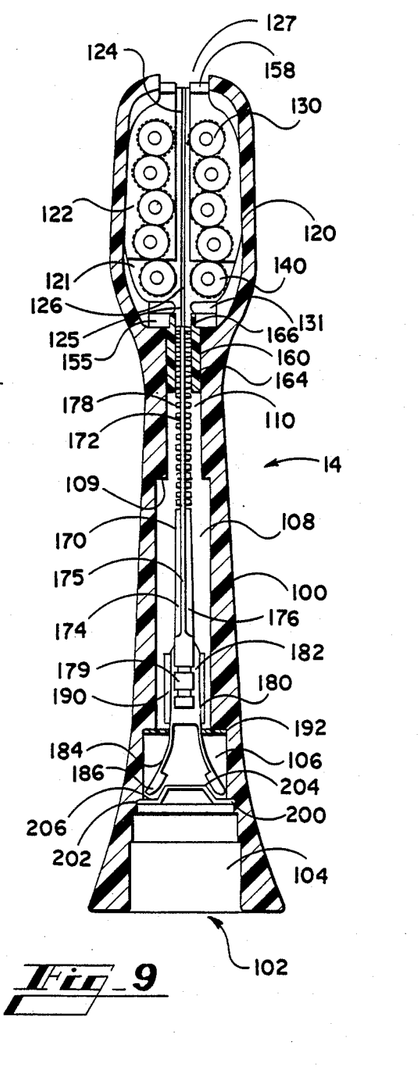
FIG. 9 is a front vertical cross sectional view of the head mechanism shown in FIG. 4 in the unlocked position, removed from the base.

As shown best in FIGS. 3 and 9, the removable head mechanism 14 comprises a hollow housing 100 having an interior cavity 102 molded in particular shapes creating connected chambers 104, 106, 108, 110, and 120 which accommodate the various pieces that make up the head mechanism. A base-receiving chamber 104 is the same "D" shape in cross section as the neck 20 of the base 12 and is designed to fit snugly over the neck 20 of the base creating a friction fit connection. In the preferred embodiment of the present invention, as a further aid in connecting the head housing 100 to the base 12, the round headed screw 25 is slidably received into an elongate slot 103 formed through the wall of the head housing, shown best in FIGS. 1 and 3. A circular opening 105, shown in FIGS. 3 and 6, is formed intermediate the ends of the slot 103, such that the slot 103 allows the housing 100 to spread and receive the screw head 25 until the screw head becomes seated in the opening 105.

Returning to FIG. 9, immediately adjacent to the base-receiving chamber 104 is a cylindrical collet chamber 106 having a slightly smaller diameter than the interior dimension of the chamber 104. Adjacent to the collet chamber is a cylindrical sleeve chamber 108 having a smaller diameter than the collet chamber 106, followed by a cylindrical rack chamber 110 having the smallest diameter of the chambers. A shoulder or ridge 109 is formed where sleeve chamber 108 meets rack chamber 110. The rack chamber 110 opens into gear chamber or recess 120 which is of a size and shape large enough to contain a number of rotatable circular gears 130 and 140. Circular gears 130 are the driven gears whereas gears 140 are the drive gears as will be explained in greater detail below.

As best shown in FIGS. 5, 6, 7, and 9, the gear chamber 120 defines a floor 121 from which protrude a pair of bearing platforms 122 separated by an elongate channel 124. An opening in the lower endwall 131 of the gear chamber 120 defines an entrance 125. The bearing platforms begin at a point spaced apart from the entrance 125 to the gear chamber 120 from the rack chamber 110. At the entrance 125 to the gear chamber, a groove 126 is formed in the floor 121 of the gear chamber 120. The groove 126 continues along the floor 121 within the elongate channel 124. Prior to the entrance 125, the rack chamber 110 narrows to form a throat 112 for a purpose described below.

Figure 4:
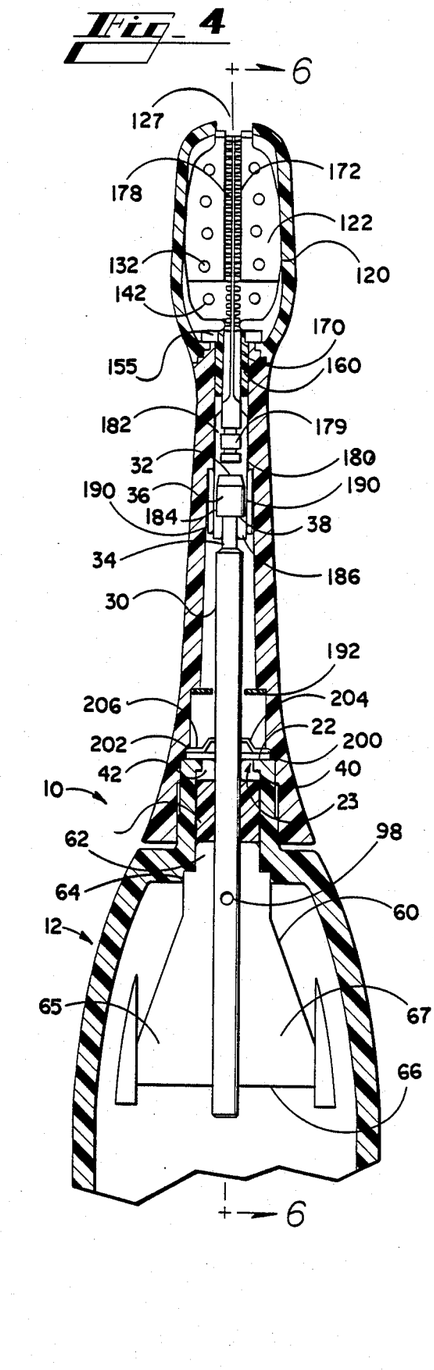
FIG. 4 is a front vertical cross sectional view of the apparatus of FIG. 1 with the base drive shaft in the extended position.

Each of the bearing platforms 122 defines a plurality of staggered cylindrical bores 132, shown best in FIG. 4, for receiving the driven gears 130. When inserted into the bores 132, adjacent gears 130 mesh with one another in driving engagement. The floor 121 between the bearing platforms and the entrance 125, on opposite sides of the groove 126, defines a pair of cylindrical bores 142 for receiving the gears 140.

At the upper end of the head mechanism 14, a slot 127 is cut out of the wall of the gear chamber 120, as shown in FIGS. 4, 5, 6, and 9. Below the slot 127, a notch 128, shown only in FIG. 6, is formed in the outer wall of the head mechanism housing 100. The slot 127 and notch 128 receive elements of a gear chamber cover 150, as described below.

Figure 8:
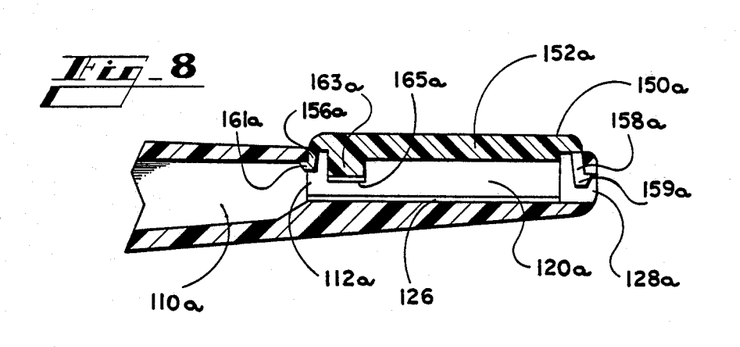
FIG. 8 is a perspective view of a second embodiment of the upper portion of the head mechanism with portions broken away to show interior detail.

In an alternative embodiment of the present invention shown in FIG. 8, a notch 128a is formed in the inner wall of the upper end of the head mechanism housing 100. This notch 128a receives elements of a gear chamber cover 150a, as described below.

As shown best in FIG. 3, each circular gear 130 has an axis of rotation perpendicular to the floor 121 of the gear chamber 120, and has a lower shaft 134 which fits into one of the cylindrical bores 132 formed in the bearing platforms 122. As each gear rotates, the cylindrical bore 132 provides a bearing for the lower shaft 134 of the gear 130. Each gear also has an upper collar 136 extending from the opposite surface of the gear, which holds a tuft of filaments 138, shown in FIG. 6, of the type shown in application Ser. No. 743,100. It will be understood that the tufts 138 comprise work-engaging members and could be replaced by buffing, polishing, grinding or other tools.

Each circular driving gear 140 also has an axis of rotation perpendicular to the floor 121 of the gear chamber 120, and has a lower shaft which fits into the cylindrical bores 142 formed in the floor 121. As each gear rotates, the cylindrical bore 142 provides a bearing for the lower shaft of the gear 140. Each gear also has an upper collar 146 extending from the opposite surface of the gear, which holds a tuft of filaments 148. The height of the gears 140 is sufficient so that the teeth of each gear extend from approximately the level of the floor 121 to a height sufficient to mesh with one of the gears 130 mounted on one of the bearing platforms 122. As will be described below, only the gears 140 engage the driving apparatus within the chambers of the head mechanism 14.

Figure 7:
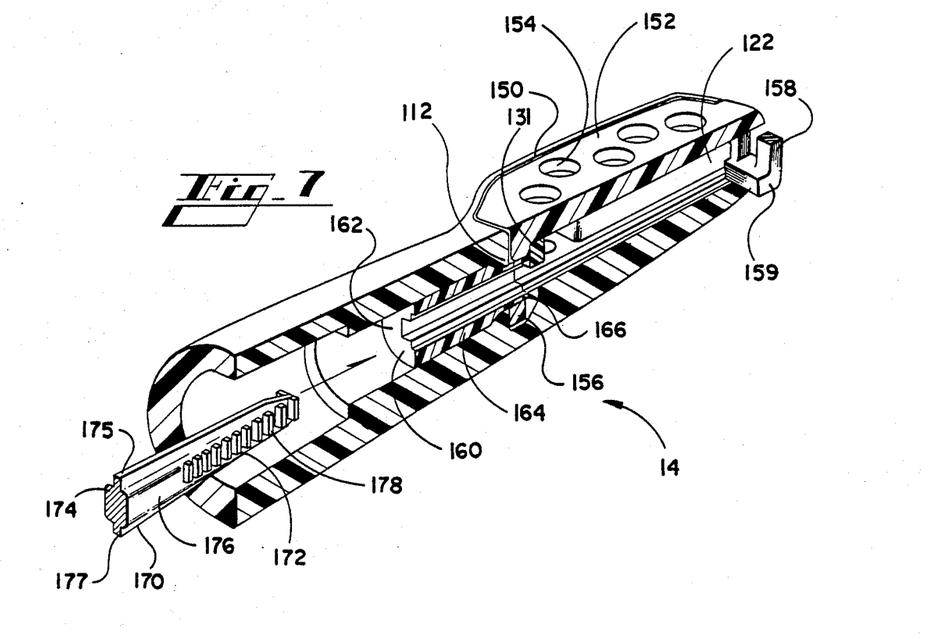
FIG. 7 is a perspective view of the upper portion of the head mechanism with portions broken away to show interior detail.

A gear chamber cover 150, shown in FIGS. 3, 6, and 7, provides a removable cover for the gear chamber 120 and maintains the gears 130 and 140 within the chamber 120. The cover 150 includes a brush plate 152, which defines a plurality of cylindrical openings 154 formed through the plate 152 aligned with the gear collars 136 and 146 of the gears 130 and 140. When the plate 152 is placed in position covering the chamber 120, the gear collars are rotatably received within the openings 154 which provide bearings for the collars 136 and 146. The tufts 138 and 148 extend through the openings 154 and protrude outwardly for engaging a surface to be cleaned, such as a person's teeth.

At the lower end of the brush plate 152, a lower tab 156 extends at right angles from the brush plate into a slot 155 defined by the lower endwall 131 of the gear chamber 120 and the throat 112. The tab 156 defines an opening 157 aligned with the entrance 125 to the gear chamber 120 and the throat 112 of rack chamber 110. At the upper end of the brush plate 152, an upper tab 158 extends at right angles from the brush plate to fill the slot 127. A locking member 159 extends from the end of the tab 158 to engage the notch 128 and retain the upper end of the cover 150 in position over the gear chamber 120. Preferably, the cover 150 is formed of a flexible material, such as a resilient plastic, so that the locking member 159 can be snapped into and out of the notch 128.

In the alternative embodiment shown in FIG. 8, two identical posts 158a, one of which is shown, extend downwardly at right angles from the upper end of the brush plate 152a. A locking member 159a extends from the end of each post to engage the notch 128a formed in the interior wall. A tab 156a extends at right angles from the lower end of the brush plate 152a. A locking member 161a extends from the tab 156a and engages the throat 112a of the rack chamber 110a when the gear chamber cover 150a is positioned over the gear chamber 120a.

In the preferred embodiment of the present invention, a cylindrical rack guide 160 having a cross-shaped central bore 162 passing through a body portion 164 and a collar 166 can be inserted into the interior cavity 102 of the head mechanism 14. The collar 166 extends upwardly from the body 164 so that the collar 166 fits tightly into the throat 112 of the rack chamber 110 and extends into the entrance 125 to the gear chamber 120 and matingly through the opening 157 of the lower tab 156, thus further securing the cover 150 to the gear chamber 120. As shown in FIG. 8 and described below, an alternative embodiment of the present invention does not utilize the rack guide 160. Rather, the locking members 159a and 161a, described above, secure the gear chamber cover 150a in place.

Referring further to FIGS. 3 and 9, a head drive shaft 170, slidably mounted within the sleeve chamber 108 and the rack chamber 110, is provided for operating the gears 140. The head drive shaft 170 comprises an elongate rack 172 at the uppermost end 173 of the rack 172. The rack 172 is cross-shaped in cross section, defining four elongate ribs 174, 175, 176, and 177, oriented at right angles to one another. Beginning at the end 173 of the rack, left and right ribs 174 and 176 form rack teeth 178 extending along the drive shaft 170. The shape of the entire rack 172 corresponds to the cross shape of the rack guide 160 allowing slidable entry of the rack 172 into the gear chamber 120 through the rack guide 160. The rack guide 160 therefore assures that the rack 172 enters the gear chamber 120 in the correct orientation so that the rack 172 properly engages the gears 140. The gears 140 are spaced apart within the gear chamber 120 by a distance such that as the rack 172 enters the gear chamber 120, the rack teeth 178 of the ribs 174 and 176 operatively engage both of the gears 140 adjacent to the floor 121. Thus, axial movement of the head drive shaft 170 and rack 172 causes the drive gears 140 to rotate, and such rotation in turn rotates the driven gears 130.

In the alternative embodiment shown in FIG. 8, a grooved bar 163a extends downwardly from the lower surface of the brush plate 152a. A groove 165a in the bar 163a engages the upper rib 175 of the rack 172 when the brush plate is secured over the gear chamber 120a much in the same manner as the rack guide 160. There is thus no need for a rack guide in the alternative embodiment.

It will be understood by those skilled in the art that the rack 170 may be cylindrically shaped with rack teeth 178 continuously around the entire perimeter of the rack.

At the lowermost end of the rack 172 of the preferred embodiment, a notched portion 179, shown best in FIG. 9, is molded into a cylindrical body portion 182 of a collet 180. The collet is preferably molded from flexible plastic or the like so that it can assume either a locked or an unlocked position as described below. Four flexible arms 184 extend downwardly from the body portion 182 and radiate outwardly in the unlocked position. The arms terminate in inwardly extending feet 186, which lie outside the radial position of the cylindrical surface of the body portion 182 when the collet is in the unlocked position.

Figure 5:
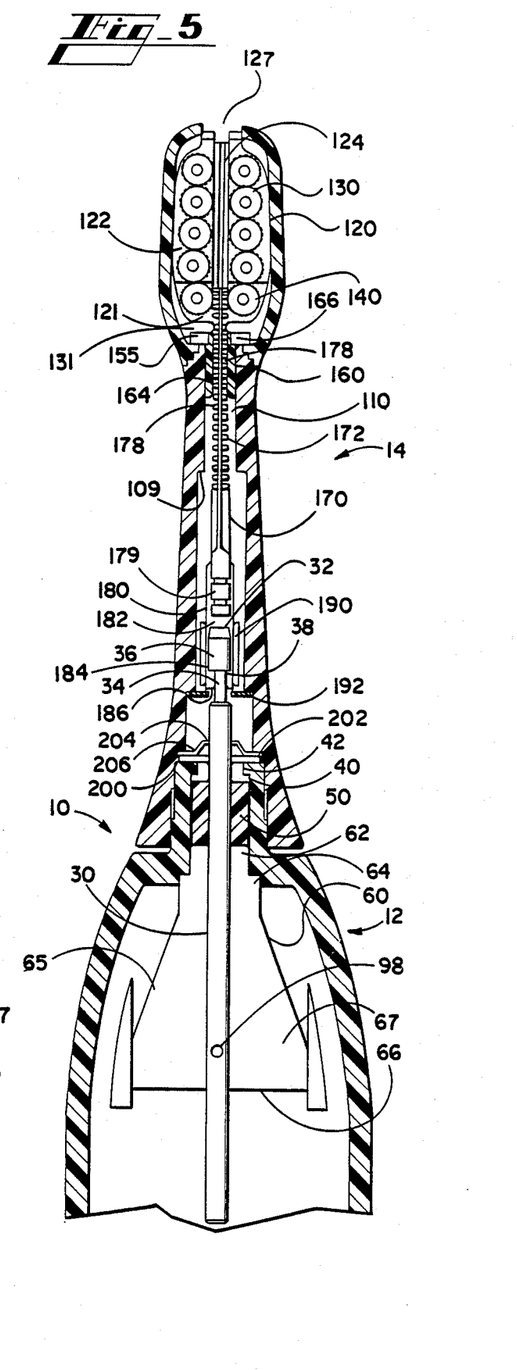
FIG. 5 is a front vertical cross sectional view of the apparatus of FIG. 1 with the base drive shaft in the retracted position and showing the gears which drive tufts of filaments.

A sleeve 190 comprises a hollow cylinder slidably received around the body portion 182 of the collet 180. The external diameter of the sleeve is small enough to slide freely within the sleeve chamber 108, but is too large to pass the shoulder 109 into rack chamber 110. In the unlocked position, the sleeve 190 surrounds the collet at its cylindrical body portion 182. When the head mechanism 14 is locked onto the base 12, the sleeve 190 surrounds and compresses the flexible arms 184 of the collet 180 as shown in FIGS. 4 and 5.

A sleeve retainer ring 192 is press fit into the housing 100 at the upper end of the collet chamber 106. As shown in FIGS. 3 and 9, the sleeve retainer 192 of the preferred embodiment of the present invention is circular in shape with a central bore 194 through which the head drive shaft 170 and the body portion 182 of the collet 180 can pass. The diameter of the sleeve retainer 192 is such that it is too large to enter the sleeve chamber 108, but small enough to be frictionally retained horizontally within the collet chamber 106, adjacent to the sleeve chamber 108. It will be seen from FIG. 9 that the sleeve 190 and sleeve retainer 192 can be placed over the drive shaft 170 before the shaft 170 is inserted into the cavity 102. The retainer ring 192 can then be press fit into the wall of the cavity as shown while surrounding the head drive shaft 170 or the collet 180. Alternately, the sleeve 190 can be inserted into the sleeve chamber 108, the retainer ring 192 press fit into place, and the shaft 170 inserted through the retainer ring and then through the sleeve.

After the insertion of the head drive shaft 170, a collet retainer ring 200 is press fit into an annular notch 202 in the wall of the cavity 102 between the base receiving chamber 104 and the collet chamber 106. The collet retainer 200 comprises a dome shaped member 204 having an annular brim 206 extending outwardly from the dome shaped member 204. A central bore 208 is formed in the center of the dome shaped member, which preferably extends upwardly into the collet chamber 106 as the brim 206 is press-fit into the annular notch 202. In the unlocked position of the collet as shown in FIG. 9, the flexible arms 184 lie on the exterior of the dome 204 of the collet retainer ring 200. It will be understood that the collet retainer ring could be formed in alternate shapes so long as the collet is prevented from falling out of the housing 100 and the base drive shaft 30 can freely pass into the collet chamber 206. In the preferred embodiment shown, the sloped surface of the dome shaped member 204 can assist in removing the feet 186 from the shoulder 38 of the base drive shaft 30 if there is any tendency of the feet to adhere to the shoulder 38 after the sleeve has been slidably removed from the arms 184 of the collet 180, as described below.

Figure 10:
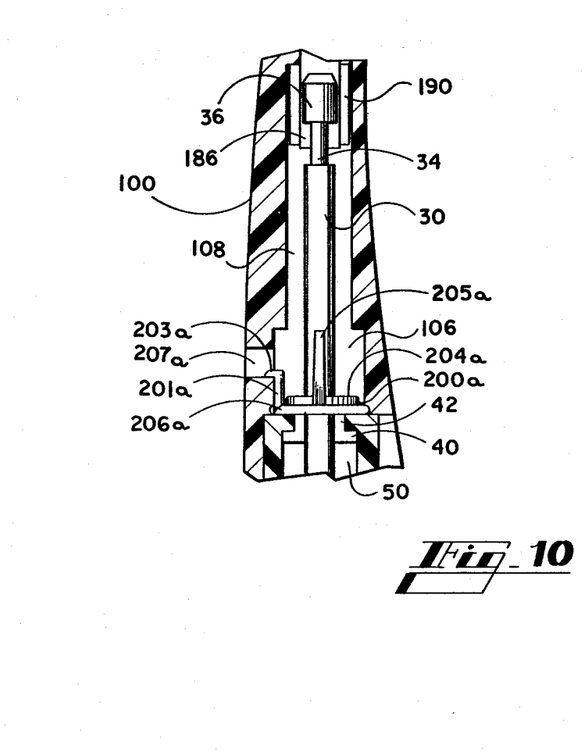
FIG. 10 is a side vertical cross sectional view of an alternate embodiment of the middle portion of the head mechanism of the invention, with the base drive shaft in the extended position.
Figure 11:
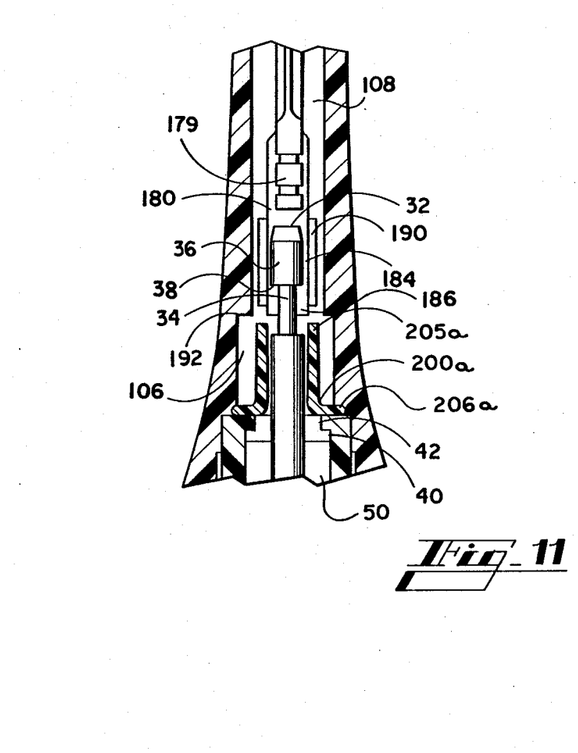
FIG. 11 is a front vertical cross sectional view of an alternate embodiment of a middle portion of the head mechanism of the invention, with the base drive shaft in the retracted position.

In an alternative embodiment, shown in FIGS. 10 and 11, a modified construction of a collet retainer ring 200a is shown. A tab 201a extends upwardly at right angles from the rear portion of the brim 206a of the collet retainer ring 200a. A locking member 203a extends outwardly from the upper end of the tab to engage an indentation 207a which may be formed in the rear wall of collet chamber 106. In addition, a pair of posts 205a extend upwardly at right angles from the brim 206a and dome shaped member 204a on either side of the central bore as shown best in FIG. 11. The posts 205a aid in removing the sleeve 190 from the flexible arms 184 of the collet 180 when the removable head mechanism 14 is disengaged from the base 12. When used, the retainer ring 200a replaces the collet retainer ring 200, and the sleeve retainer ring 192 of the previous embodiment.

Operation

The removable head mechanism 14 is engaged and disengaged with the base 12 by the following procedure. Although the base drive shaft 30 may extend an indefinite distance from the neck 20 when the power switch 18 is operated to turn off power to the motor 70, its position is not critical to engaging or disengaging the removable head mechanism 14. To engage the head mechanism with the base, the head mechanism is grasped and moved downwardly toward the base so that the neck 20 begins to enter the base receiving chamber 104. The slot 103 moves over the round headed screw 25 until the screw 25 seats within the circular opening 105. The head mechanism 14 is firmly attached to the base 12 when the flat upper surface 22 of the neck 20 of the base comes in contact with the flat lower surface of the collet retaining ring 200.

The base drive shaft 30 is inserted through the collet retainer ring 200 into the collet chamber 106. The tip 36 of the base drive shaft 30 is received between the outwardly radiating flexible arms 184 of the collet 180 as the neck 20 of the base is brought into a mating relationship with the base receiving chamber 104 of the head mechanism 14. If the base drive shaft is sufficiently extended, for example as shown in FIG. 4, the action of inserting the base drive shaft will move the head drive shaft upwardly within the sleeve chamber 108 until the sleeve 190, carried by the body portion 182 of the collet 180, engages the shoulder 109 formed between the sleeve chamber 108 and the rack chamber 110. Further insertion pushes the sleeve over the arms 184 of the collet, causing the feet 186 to move inwardly into engagement with the shoulder 38 of the base drive shaft 30. If, on the other hand, the base drive shaft 30 is initially in a lower position, such as shown in FIG. 5, insertion of the neck 20 into the base receiving chamber 104 will not fully engage and lock the head mechanism 14 to the base 12. However, when the power switch 18 of the base 12 is engaged to operate the motor 70, the base drive shaft 30 moves axially to the extended position shown in FIG. 4. The sleeve 190 is carried with the collet 180 of the head drive shaft 170 until it abuts the shoulder 109 at the uppermost portion of the sleeve chamber 108. The sleeve 190 is then held stationary as the base drive shaft pushes the collet 180 of the head drive shaft further into the rack chamber 110. The flexible arms 184 of the collet 180 flex inwardly as they enter the sleeve 190 and each foot 186 moves into the annular indented region 34 of the base drive shaft at the shoulder 38 in a locked position as shown in FIGS. 4 and 6.

Regardless of whether locking occurs during manual assembly of the head mechanism onto base or when the power is turned on, as the drive shaft moves upwardly during the locking procedure, the rack 172 slides through the rack guide 160 and enters the gear chamber 120. The rack teeth 178 engage the gears 140 and the rack 172 slides along the channel 124 toward the slot 127.

Once the head mechanism has been locked onto the base, the head drive shaft 170 reciprocates the axial movements of the base drive shaft 30. During such movement, the sleeve 190 remains in place compressing the arms 184 of the collet 180. The tip 36 of the base drive shaft 30 remains entrapped by the arms 184 and the feet 186 and moves with the head drive shaft 170 from an uppermost position shown in FIG. 4 to a lowermost position shown in FIG. 5, according to reciprocation of the crank arm 90. The rack 172 reciprocates along the channel 124, causing the gears 140 to alternately rotate and counter-rotate. This in turn causes a similar sequence of rotation of the gears 130. Thus, the tufts of filaments 138 and 148 are caused to rotate as described in application Ser. No. 743,100, creating a cleaning action particularly useful in removing dental plaque.

To disengage the head mechanism 14 from the base 12, the head mechanism is grasped and moved upwardly away from the base so that the base receiving chamber 104 is lifted from the neck 20. As the head mechanism is thus moved, the round headed screw 25 is dislodged from the circular opening 105 and is moved along the slot 103 until released from the head housing 100.

The base drive shaft 30 is unlocked from the collet 180 of the head drive shaft 170 by the release of the arms 184 from the sleeve 190. If the base drive shaft 30 is sufficiently retracted, for example as shown in FIG. 5, the sleeve 190 is positioned adjacent to the sleeve retainer ring 192. Upward movement of the head mechanism causes the withdrawal of the base drive shaft 30, surrounded by the arms 184 of the collet 180, from the sleeve 190. If the base drive shaft is not sufficiently retracted, the upward movement of the head mechanism 14 causes the sleeve to freely slide downwardly within the sleeve chamber 108 until it engages the sleeve retainer ring 192. Further upward movement of the head mechanism causes the withdrawal of the base drive shaft 30, surrounded by the arms 184 of the collet 180, from the sleeve 190. The sleeve is retained by the sleeve retaining ring 192 as the base drive shaft 30 and attached collet 180 descend through the central bore 194 of the sleeve retaining ring 192. The withdrawal action causes the flexible arms 184 to regain their outwardly radiating unlocked position, shown in FIG. 9.

In the alternate embodiment shown in FIGS. 10 and 11, the posts 205a engage the sleeve 190 as upward movement of the head mechanism causes the withdrawal of the base drive shaft 30, surrounded by the arms 184 of the collet 180, from the sleeve 190. The posts 205a perform the same function as the sleeve retaining ring 192 found in the first embodiment and thus replace the sleeve retaining ring. FIG. 11 shows the sleeve 190 about to engage the posts 205a.

In the preferred embodiments shown, the sloped surface of the dome shaped members 204 and 204a of the collet retainer rings 200 and 200a aids in the removal of the feet 186 from the shoulder 38 of the base drive shaft 30. As the flexible arms 184 are withdrawn from the sleeve 190, the gradually increasing external diameter of the domed shaped members 204 and 204a provides a wedge-like function, prying the feet 186 from the shoulder 38 if there is any tendency for the feet to adhere to the shoulder.

Further upward movement of the head mechanism 14 causes the base drive shaft 30 to descend through the central bore 208 of the collet retainer ring 200. However, the outwardly radiating flexible arms 184 of the collet cannot pass through the central bore 208 of the collet retainer ring, preventing the downward passage of the head drive shaft 170 through the central bore 208. The collet is thus retained within the collet chamber 106, the sleeve is retained within the sleeve chamber 108, and the rack 172 remains partially within the sleeve chamber and partially within the rack chamber 110 as shown in FIG. 9, so that a portion of the rack remains within the rack guide 160.

Once the base drive shaft 30 has been unlocked from the collet 180 of the head drive shaft 170, further upward movement of the head creates a total separation of the base 12 from the head mechanism 14.

Thus, it will be seen that the present invention provides a removable head mechanism with its own axial drive shaft and a novel means for automatically connecting and disconnecting the head drive shaft to the power driven shaft of a base which serves as a handle for manipulating the tool as a whole.

While this invention has been described with particular reference to preferred embodiments thereof, it will be understood that variations and modifications can be made without departing from the spirit and scope of the invention as described hereinbefore and as defined in the appended claims.

We claim:

1. A removable head mechanism for use with a base having a base drive shaft extending therefrom, comprising:
    a hollow housing;
    a head drive shaft slidably mounted for longitudinal movement within said housing; and
    means for connecting said base drive shaft to said head drive shaft in locking relationship responsive to axial movement of said base drive shaft into housing.

2. The removable head mechanism of claim 1, wherein said base comprises:
    means for driving said base drive shaft in a longitudinal direction:
    a bearing through which said base drive shaft passes; and
    a seal through which said base drive shaft passes.

3. A removable head mechanism, for use with a base having a base drive shaft extending therefrom, said base drive shaft defining a shoulder spaced inwardly from the end of said shaft, said head mechanism comprising:
    a hollow housing;
    a head drive shaft slidably mounted within said housing;
    a flexible arm mounted for movement with said head drive shaft and defining an inwardly extending foot at the end of said arm; and
    locking means for selectively moving said arm between an unlock position radially outwardly of the shoulder defined by said base drive shaft and a lock position in which said foot engages said shoulder when said head mechanism is mounted on said base.

4. The removable head mechanism of claim 3, further comprising means for operating said locking means responsive to axial movement of said base drive shaft into said housing.

5. The removable head mechanism of claim 4, wherein said locking means comprises a hollow sleeve, operable to slidingly receive said arm so as to cause said foot to engage said shoulder of said base drive shaft.

6. The removable head mechanism of claim 5, wherein said housing defines an interior ridge positioned in the path of said hollow sleeve, said axial movement of said base drive shaft causing said hollow sleeve to engage said ridge such that said arm slidably enters said hollow sleeve.

7. The removable head mechanism of claim 6, further comprising unlocking means for selectively moving said arm between a lock position in which said foot engages said shoulder and an unlock position radially outwardly of the shoulder defined by said base drive shaft.

8. The removable head mechanism of claim 7, wherein said unlocking means comprises a sleeve retainer defining an opening through which said head drive shaft passes; said opening being smaller than the external diameter of said sleeve; said sleeve retainer being positioned so that, as said head mechanism is detached from said base, said sleeve abuts said sleeve retainer and said sleeve is slidably removed from said arm, releasing said foot from said shoulder of said base drive shaft.

9. The removable head mechanism of claim 3, wherein said housing defines a recess for receiving a work-engaging member operatively connected to said head drive shaft, and further comprising:
    a plate for covering said recess, said plate defining a bearing for receiving said work-engaging member, and a tab extending across the path of movement of said head drive shaft, said head drive shaft being received for movement through an opening defined in said tab.

10. The removable head mechanism of claim 9, further comprising:
    a shaft guide sleeve slidably receiving said head drive shaft and defining a collar positioned to be matingly received within said opening in said tab.

11. The removable head mechanism of claim 10, wherein said work-engaging member comprises a rotatable tuft of filaments.

12. The removable head mechanism of claim 10, wherein said recess includes a plurality of said work-engaging members, and wherein said plate defines a plurality of said bearings;
said work-engaging members comprising a plurality of gears received within said plurality of bearings in said plate, each of said gears carrying a tuft of filaments; and
said head drive shaft defining a rack member operably connected to said gears.

13. The removable head mechanism of claim 12, further comprising means for connecting said rack member and said gears such that reciprocation of said rack member causes said tufts to rotate in one direction, and then causes said tufts to counter-rotate in an opposite direction.

14. The removable head mechanism of claim 3, wherein said base comprises:
means for driving said base drive shaft;
a bearing through which said base drive shaft passes; and
a seal through which said base drive shaft passes.

15. The removable head mechanism of claim 14, further comprising means for operating said locking means responsive to axial movement of said base drive shaft into said housing.

16. The removable head mechanism of claim 15, wherein said locking means comprises a hollow sleeve, operable to slidingly receive said arm so as to cause said foot to engage said shoulder of said base drive shaft.

17. The removable head mechanism of claim 16, wherein said housing defines an interior ridge positioned in the path of said hollow sleeve, said axial movement of said base drive shaft causing said hollow sleeve to engage said ridge such that said arm slidably enters said hollow sleeve.

18. The removable head mechanism of claim 17, further comprising un lock ing means for selectively moving said arm between a lock position in which said foot engages said shoulder and an unlock position radially outwardly of the shoulder defined by said base drive shaft.

19. The removable head mechanism of claim 18, wherein said unlocking means comprises a sleeve retainer defining an opening through which said head drive shaft passes; said opening being smaller than the external diameter of said sleeve; said sleeve retainer being positioned so that, as said head mechanism is detached from said base, said sleeve abuts said sleeve retainer and said sleeve is slidably removed from said arm, releasing said foot from said shoulder of said base drive shaft.

20. The removable head mechanism of claim 3, further comprising unlocking means for selectively moving said arm between a lock position in which said foot engages said shoulder and an unlock position radially outwardly of the shoulder defined by said base drive shaft.

21. An apparatus for transmitting powered motion to an operating member, said apparatus comprising:
a base including a base drive shaft extending therefrom;
means mounted in said base for reciprocating said base drive shaft axially;
a removable head mechanism including a head drive shaft slidably mounted for axial movement within a hollow housing and operatively associated with said operating member; and,
locking means for connecting said base drive shaft to said head drive shaft actuated solely by axial movement of said base drive shaft into said hollow housing of said head mechanism.

22. An apparatus for transmitting powered motion to an operating member, said apparatus comprising:
a base including a base drive shaft extending therefrom, defining a shoulder spaced inwardly from the end of said base drive shaft;
a removable head mechanism including a head drive shaft slidably mounted within a hollow housing;
a flexible arm mounted for movement with said head drive shaft and defining an inwardly extending foot at the end of said arm; and
locking means for selectively moving said arm between an unlock position radially outwardly of the shoulder defined by said base drive shaft and a lock position in which said foot engages said shoulder when said head mechanism is mounted on said base.

23. The apparatus of claim 22, further comprising means for operating said locking means responsive to axial movement of said base drive shaft into said housing.

24. The apparatus of claim 23, wherein said locking means comprises a hollow sleeve, operable to slidingly receive said arm so as to cause said foot to engage said shoulder of said base drive shaft.

25. The apparatus of claim 24, wherein said housing defines an interior ridge positioned in the path of said hollow sleeve, causing the retention of said hollow sleeve as axial movement of said base drive shaft causes said head drive shaft to slidably enter said hollow sleeve causing said foot to engage said shoulder of said base drive shaft.

26. The apparatus of claim 25, comprising unlocking means for selectively moving said arm between a lock position in which said foot engages said shoulder and an unlock position radially outwardly of the shoulder defined by said base drive shaft.

27. The apparatus of claim 26, wherein said unlocking means comprises a sleeve retainer with an opening larger than said head drive shaft; said opening being smaller than the external diameter of said sleeve; said sleeve retainer being positioned so that, as said head mechanism is detached from said base, said sleeve abuts said sleeve retainer and said sleeve is slidably removed from said arm, releasing said foot from said shoulder of said base drive shaft.

28. An apparatus for transmitting powered motion to a work-engaging member, said apparatus comprising:
a housing defining a recess therein;
a work-engaging member positioned within said recess;
a drive shaft;
means for operably connecting said drive shaft to said work-engaging member;
a plate for covering said recess, said plate defining a bearing for receiving said work-engaging member; and
a tab extending from said plate across the path of movement of said drive shaft, said drive shaft being received for movement through an opening defined in said tab.

29. The apparatus of claim 28, further comprising:
a shaft guide sleeve slidably receiving said drive shaft and defining a collar positioned to be matingly received within said opening in said tab.

30. The apparatus of claim 29, wherein said work-engaging member comprises a rotatable tuft of filaments.

31. The apparatus of claim 30, wherein said recess includes a plurality of said work-engaging members, and wherein said plate defines a plurality of said bearings;
said work-engaging members comprising a plurality of gears received within said plurality of bearings in said plate, each of said gears carrying a tuft of filaments; and
said drive shaft defining a rack member operably connected to said gears.

32. A method of connecting a base, having a base drive shaft extending therefrom, to a removable head mechanism, comprising the steps of:
axially inserting said base drive shaft into a hollow housing of said head mechanism, said base drive shaft being adapted for axial movement;
axially extending said base drive shaft to a predetermined extended position; and
responsive solely to axial movement of said base drive shaft, locking said base drive shaft to a head drive shaft slidably mounted for axial movement within said housing of said head mechanism.

33. The method of claim 32, wherein said base drive shaft is axially extended to said predetermined extended position prior to said step of axially inserting said base drive shaft into said hollow housing.

34. A method of connecting a base, including a base drive shaft extending therefrom, to a removable head mechanism, comprising the steps of:
inserting said base drive shaft into a hollow housing of said head mechanism, said base drive shaft defining a shoulder spaced inwardly from the end of said shaft; and
responsive to axial movement of said base drive shaft, locking said base drive shaft to a head drive shaft slidably mounted within said housing, said head drive shaft including a flexible arm mounted for movement with said head drive shaft, said flexible arm defining an inwardly extending foot at the end of said. arm, so that said foot of said flexible arm of said head drive shaft is inserted onto said shoulder of said base drive shaft.

* * * * *